United States Patent
Petersen et al.

(10) Patent No.: US 6,939,299 B1
(45) Date of Patent: Sep. 6, 2005

(54) IMPLANTABLE CONTINUOUS INTRAOCULAR PRESSURE SENSOR

(76) Inventors: Kurt Petersen, 1190 Borregas Ave., Sunnyvale, CA (US) 94086; Gregory T. A. Kovacs, 105 Peter Coutts Cir., Stanford, CA (US) 94305; Terence G. Ryan, 7 Chinook Ct., Palm Coast, FL (US) 32137; Leon G. Partamian, 10324 Steven Pl., Chatsworth, CA (US) 91311; David A. Lee, 730 Cricket Glen Rd., Hummelstown, PA (US) 17036

( * ) Notice: Subject to any disclaimer, the term of this patent is extended or adjusted under 35 U.S.C. 154(b) by 640 days.

(21) Appl. No.: 09/733,879

(22) Filed: Dec. 8, 2000

Related U.S. Application Data
(60) Provisional application No. 60/170,450, filed on Dec. 13, 1999.

(51) Int. Cl.$^7$ .................................................. A61B 3/16
(52) U.S. Cl. ...................... 600/398; 600/300; 600/405; 600/561; 600/587
(58) Field of Search ................................ 600/587, 398, 600/405, 561

(56) References Cited

U.S. PATENT DOCUMENTS

| | | | | |
|---|---|---|---|---|
| 3,406,681 A | * | 10/1968 | Zandman ........................ 128/2 |
| 4,003,141 A | * | 1/1977 | Le Roy .......................... 35/17 |
| 4,026,276 A | * | 5/1977 | Chubbuck ....................... 128/2 |
| 4,114,603 A | * | 9/1978 | Wilkinson .................... 128/2 R |
| 4,127,110 A | | 11/1978 | Bullara .......................... 128/2 |
| 4,147,161 A | * | 4/1979 | Ikebe et al. ................. 128/2 R |
| 4,600,013 A | * | 7/1986 | Landy et al. ............... 128/748 |
| 4,628,938 A | * | 12/1986 | Lee ............................. 128/652 |
| 5,830,139 A | | 11/1998 | Abreu ........................ 600/405 |
| 5,833,603 A | | 11/1998 | Kovacs et al. .............. 600/317 |
| 5,873,840 A | * | 2/1999 | Neff ............................ 600/561 |
| 6,115,634 A | | 9/2000 | Donders et al. .............. 607/32 |
| 6,115,636 A | | 9/2000 | Ryan ........................... 607/60 |
| 6,117,089 A | * | 9/2000 | Sinha .......................... 600/561 |
| 6,278,379 B1 | * | 8/2001 | Allen et al. ............ 340/870.16 |
| 6,287,253 B1 | * | 9/2001 | Ortega et al. ............... 600/300 |
| 6,443,893 B1 | * | 9/2002 | Schnakenberg et al. ..... 600/398 |

OTHER PUBLICATIONS

Rosengren, L, *A system for passive implantable pressure sensors*, Sensors and Actuators A, 43, pp. 55–58, 1994.

Collins, C, *Miniature passive pressure transenor for implanting in the eye*, IEEE Trans on Bio Med. Eng., BME–14(2),pp. 74–83, 1967.

* cited by examiner

*Primary Examiner*—Henry Bennett
*Assistant Examiner*—Nihir Patel
(74) *Attorney, Agent, or Firm*—Lumen Intellectual Property Services, Inc.

(57) ABSTRACT

An implantable miniaturized pressure sensor integrates a capacitor and an inductor in one small chip, forming a resonant LC circuit having a Q value of 10 or greater. The capacitor has an upper capacitor plate and a lower capacitor plate disposed proximate thereof. The upper and lower capacitor plates are connected to one or more spiral inductor coils. The sensor is micromachined from silicon to form a thin and robust membrane disposed on top of the upper capacitor plate. The sensor is hermetically sealed and the membrane is deflected relative to the upper capacitor plate by an external fluid, gas, or mechanical pressure. The resonant frequency of the sensor can be remotely monitored and continuously measured with an external detector pick up coil disposed proximate the sensor. The sensor can be smaller than 2×2×0.5 mm and is particularly useful for intraocular applications.

41 Claims, 12 Drawing Sheets

IMPLANTABLE CONTINUOUS INTRAOCULAR PRESSURE SENSOR

CROSS-REFERENCE TO RELATED APPLICATIONS

This application is based on Provisional application 60/170,450 filed Dec. 13, 1999 which is herein incorporated by reference.

FIELD OF THE INVENTION

This invention relates generally to pressure sensors. More particularly, it relates to a remotely monitored implantable continuous intraocular pressure sensor(s).

BACKGROUND ART

Glaucoma is a potentially blinding disease, distinguished by elevated intraocular pressure (IOP), which if left untreated can lead to optic nerve damage resulting in blindness. Today's glaucoma therapy consists of mainly monitoring, and lowering the intraocular pressure by medical or surgical therapy.

Measurement of intraocular pressure in glaucoma patients is usually performed in a doctor's office, using one of the presently available external tonometers. Clinical measurement of intraocular pressure is performed by deforming the globe of the eye and correlating the force responsible for the deformation to the pressure within the eye. Both indentation and applanation tonometers deform the globe of the eye while measuring intraocular pressure. A third type of tonometer, the non-contact tonometer, measures the time required to deform the corneal surface in response to the force produced by a jet of air. The accuracy of the non-contact tonometer is diminished with higher intraocular pressures and in eyes with abnormal corneas or poor fixation.

Most tonometers require the application of a topical anesthetic following which the tonometer is applied to the corneal surface, by or under the supervision of a physician. The unequivocal need to have a highly trained professional available during intraocular measurements, in addition to the risk of corneal abrasion, reactions to topical anesthetics, and transmission of infectious agents limit the accessibility and ease of monitoring intraocular pressure in glaucoma patients.

The intraocular pressure in normal people varies throughout the day. Abnormal pressure peaks may occur at odd hours, e.g. very early in the morning, or at times when it is inconvenient to see the patient in the doctor's office and impractical to record the intraocular pressures. This fluctuation is often accentuated in people with glaucoma.

Knowledge of variations in intraocular pressure is important for the diagnosis, treatment, and eventually prognosis of glaucoma. An intraocular pressure measurement at one point in time may not tell the whole story. In patients for whom elevated intraocular pressures can not be documented during visits into the doctor's office, diurnal curves are considered to be a great value in the diagnosis and treatment of glaucoma, and to evaluate the response to glaucoma therapy during subsequent visits. The diurnal intraocular pressure curves can provide information on both peak intraocular pressure, and the range of diurnal pressure variations. Documentation of diurnal intraocular pressure variations is crucial in the study and assessment of dose response studies of anti-glaucoma medications. The need to verify and document diurnal pressure variations is especially important in patients with seemingly controlled intraocular pressures, but with progressive glaucomatous damage.

Assessing diurnal variations of intraocular pressure requires repeated measurements around the clock. Methods used include inpatient measurements, office measurements, and outpatient-hospital combinations. The major disadvantages of these latter procedures are their cost, the drastic modification introduced of the patient's normal activities, and possible introduction of exogenous factors that affect the diurnal pressure, such as in changing the normal sleep pattern, and hence possibly falsely varying the measured intraocular pressures. Another major disadvantage is the gradual reduction of the intraocular pressure induced by multiple manipulations and pressure applications on the corneal surface, which result in an iatrogenic reduction in the intraocular pressure, a phenomenon known as the "Tonography effect".

Attempts have been made to have patients or their relatives measure the intraocular pressure at home during various times of the day either to look for elevated intraocular pressures or to assess the quality of intraocular pressure control. This could be a source of corneal abrasions and infections, in addition to possibly initiating topical anesthetic abuse. Moreover, the results and accuracy of home tonometry have been highly variable.

U.S. Pat. No. 5,833,603 to Kovacs' et al. issued Nov. 10, 1998 disclosed a biosensing transponder for implantation in an organism, which includes a biosensor and a transponder. Although one embodiment describes a biosensing transponder with an implantable inductive pressure sensor to allow remote sensing and retrieval of static and dynamic pressure information, no details of the construction of the inductive sensor are provided.

An article entitled "Miniature Passive Pressure Transensor for Implanting in the Eye" by Carter C. Collins, issued by IEEE on Bio-Medical Engineering in April 1967, disclosed an intraocular pressure sensor including a pair of parallel, coaxial, flat spiral coils, which constitutes a distributed resonant circuit whose frequency varies with relative coil spacing. However, the spiral coils of the intraocular pressure sensor of Collins are produced by hand winding and hand assembly, which is both costly and inefficient.

Another article entitled "A System for Passive Implantable Pressure Sensors" by Rosengren et al., issued by Sensors and Actuators A in 1994, disclosed an implantable sensor, which is a capacitive micromachined silicon structure, together with a coil, constitutes a passive radio-frequency resonator. The coil is made up of 50 $\mu$m diameter gold wire, wound on a plastic fixture with a diameter of 5 mm. The capacitor is glued to the fixture, and the coil ends are bonded to the top and bottom surface of the capacitor. Unfortunately, this sensor has a large size of 5 mm diameter and 2 mm thickness. In addition, the device also uses hand wound coils and assembly by hand.

U.S. Pat. No. 4,127,110 to Bullara issued Nov. 28, 1978 discloses a wireless, surgically implantable pressure transducer for measuring pressure of fluid or tissue in a body chamber such as a brain ventricle of a patient suffering hydrocephalus or after head injury. The transducer includes a helical inductor coil and a capacitor connected in parallel to form a resonant L-C circuit. One of these reactive components is variable, and a bellows is mechanically connected to the variable component to vary the value of capacitance or inductance and hence the resonant frequency of the L-C circuit in response to pressure changes of fluid in which the bellows is immersed. The resonant frequency of L-C circuit is detected and measured by an external source of variable-frequency energy such as a grid-dip oscillator or a solid state equivalent. Unfortunately, the helical inductor coil needs hand winding of gold wire around a core having an outside diameter of 0.25 inch, thus the transducer has a large size.

U.S Pat. No. 4,026,276 to Chubbuck issued May 31, 1977 discloses a pressure monitoring apparatus implantable in the cranium to measure intracranial pressure. The apparatus comprises a passive resonant circuit having a natural frequency influenced by ambient pressure. The resonant circuit has inductance and capacitance capability for comparing the local environmental pressure to that of a volume of gas trapped inside the apparatus. The environmental pressure is measured by observation of the frequency at which energy is absorbed from an imposed magnetic field located externally of the cranium. However, this apparatus has a cylindrical inductance coil, which needs hand winding and hand assembly.

U.S. Pat. No. 4,628,938 to Lee issued Dec. 16, 1986 and U.S. Pat. No. 5,830,139 to Abreu issued Nov. 3, 1998 disclose non-invasive, continuous applanation tonometers including pressure sensors for measuring intraocular pressure, which is performed by deforming the globe and correlating the force responsible for the deformation to the pressure within the eye. Unfortunately, these techniques require a highly trained professional available during intraocular pressure measurements, in addition to the risk of corneal abrasion, reactions to topical anesthetics, and transmission of infectious agents.

There is a need, therefore, for an implantable intraocular pressure measuring microdevice that overcomes the above difficulties.

OBJECTS AND ADVANTAGES

Accordingly, it is a primary object of the present invention to provide a remote and miniaturized pressure sensor to continuously measure the pressure of tissue, fluid, or gas in a body chamber, or pressure of non-medical pressurized chambers or cavities.

It is another object of the present invention to provide a pressure sensor for continuous measurement of intraocular pressure for hours or days without influencing and interfering with stability of the rhythm of the individual, or iatrogenically changing the intraocular pressure.

It is a further object of the present invention to prevent unnecessary risk factors while measuring the intraocular pressure, such as damaging the corneal epithelium or introducing infections.

It is another object of the present invention to provide a pressure sensor having small size, high performance characteristics, and low manufacturing cost.

It is another object of the present invention to provide a pressure sensor that does not require an internal energy source.

It is another object of the present invention to facilitate frequent monitoring of the intraocular pressure in a patient.

SUMMARY

These objects and advantages are attained by a remote and miniaturized continuous pressure measuring sensor and an intraocular sensor system.

In accordance with the first embodiment of the present invention, a continuous pressure measuring sensor includes a pressure sensing capacitor and an inductor. The capacitor and the inductor are integrated in one small micromachined chip, which forms an inductor/capacitor resonant circuit (or resonant LC circuit) characterized by a resonant frequency. The inductor is a spiral micromachined coil made by removing selected portions of material from a conductive sheet. A first capacitor plate, the second capacitor plate, and the flat spiral inductor coil are made of metal films of Al, Au, or Cu. The spiral inductor coil is typically a flat coil that is coplanar and coaxial with the first capacitor plate, which allows the pressure sensor to be miniaturized to a size less than 2×2×0.5 mm and fabricated reliably in large batches at low cost. An alternative pressure sensor further includes another flat spiral inductor coil coplanar with the second capacitor plate. In addition, another alternative pressure sensor has a cylindrical spiral inductor coil coaxial with both capacitor plates.

The inductor and the first capacitor plate are placed on top of a deformable or even non-deformable membrane, such as a glass substrate, sealed and electrically isolated inside the sensor. The sensor further includes a deformable membrane bonded to the glass substrate and disposed-on top of the second capacitor plate. The membrane is typically made of silicon. Alternatively, the membrane is preferably made of polymer resins systems, such as Silastic, Teflon AF and polyimide (a.k.a. Kapton), using flexible circuit technology in accordance with a preferred embodiment of the present invention. Fluid can not touch the sealed metal plates, so it can not form an electrical connection, which may provide an accurate pressure signal (if fluid touched the metal plate it would drastically lower the Q of the circuit, making measurements difficult if not impossible, or if fluid got between plates there would be no pressure difference to deflect the plates). Fluid pressure deflects the membrane and the second capacitor plate. The higher the pressure difference, the larger the deflection. These pressure-induced motions of the membrane change the capacitance value, thus, change the resonant frequency of the LC circuit. An increase in pressure causes an increase in capacitance, which causes a decrease in resonant frequency. The pressure sensor is a remote pressure sensing device and does not require an internal or external energy source. The pressure sensor is coated with medical-grade biocompatible coating prior to implantation.

According to a second embodiment of the present invention, the pressure sensors are made by flexible circuit technology. The candidate polymer resins systems, such as Silastic, Teflon AF and polyimide, are spun cast onto 4-inch silicon wafers allowing the flexibility of construct polymer films from about 5 microns to about 100 microns thick. The silicon wafers are coated with a thick release layer (like Al) that allows the films to be easily removed from the silicon support wafers after processing is completed. A thin metal adhesion layer, typically made of Ti and Au, is sputter deposited onto the polymer film coated wafers. A thick photoresist about 25–100 microns is spun cast onto the seed layer and patterned to form the coil and capacitor plates of the sensor. Wafers are placed into an Au plating bath and Au is selectively plated up through the openings in the resist. The resist is stripped and the thin seed layer is etched away from the areas between the plated metal coils and capacitor plates. A thin overcoating of a passivating material can be deposited at this point, choices range from spun cast polymers to plasma enhanced chemical vapor deposited silicon nitride or a fluoropolymer. A thin masking layer is deposited over the wafer and patterned into the final dumb-bell shape of the unfolded sensor. The polymer base layer is etched away exposing the release layer below it. Release layer is removed and all of the unfolded sensors are freed from the silicon wafer. Each device is placed into an assembly jig and the spacer layer is adhesively bonded to the lower lobe. Adhesive is placed over the upper lobe and it is folded over onto the lower lobe thus completing the sensor's construction.

Pressure sensors of the types depicted in the first and second embodiments are configured to measure intraocular or intra-tissue pressures. The intraocular pressure sensor (IOP) sensor is placed inside an eye such as in an anterior chamber, posterior chamber, vitreous cavity, or within tissues and intercellular spaces in the eye. The IOP sensor may also be placed on an eyeball's surface, in an orbital space, or within tubes attached to the eye or its contents, in or along with drainage tubes, shunts, or setons. In addition, the IOP sensor may be incorporated with contact lenses in contact with the cornea or sclera, in order to continuously monitor and convert the tactile pressure to the intraocular pressure. The IOP sensor of the present invention may also be incorporated into surgical equipment such as extraction units, phacoemulsification or irrigation aspiration systems, or with refractive surgery or keratomileusis procedures including laser assisted procedures, where pressure is applied to the eye during the procedure.

A pressure sensor may be incorporated into a pressure measurement system. A pressure measurement system includes a pressure sensor, an external detector pick-up coil disposed proximate the sensor. The system further includes an electronic interface module coupled to the external detector pick-up coil, and a data analysis computer coupled to the electronic interface module. The external detector pick-up coil is a flat, wound coil having a diameter of about 2 cm, and is placed within about one centimeter of the pressure sensor. In case the pressure measuring system is used to measure the intraocular pressure, the external detector pick-up coil may be placed in a device that can be worn safely, comfortably and conveniently without disturbance of vision or ocular physiology. For example, the pick-up coil may be mounted within a pair of eyeglasses.

A method of continuously measuring intraocular pressure using the above measurement system is also described. A pressure sensor having a LC circuit is inserted into an eye. The resonant frequency of the LC circuit is detected by applying a signal to the adjacent external detector pick-up coil. The signal applied to the external detector pick-up coil is varied in frequency until the resonant frequency of the sensor is located. The signal applied is generated by the electrical interface module, which is controlled by a data analysis computer. Therefore the resonant frequency of the sensor is detected by the electronic interface module and is transmitted to the data analysis computer for analysis and calibration. In this way, the intraocular pressure is measured on a continuous basis.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Figure 1A:
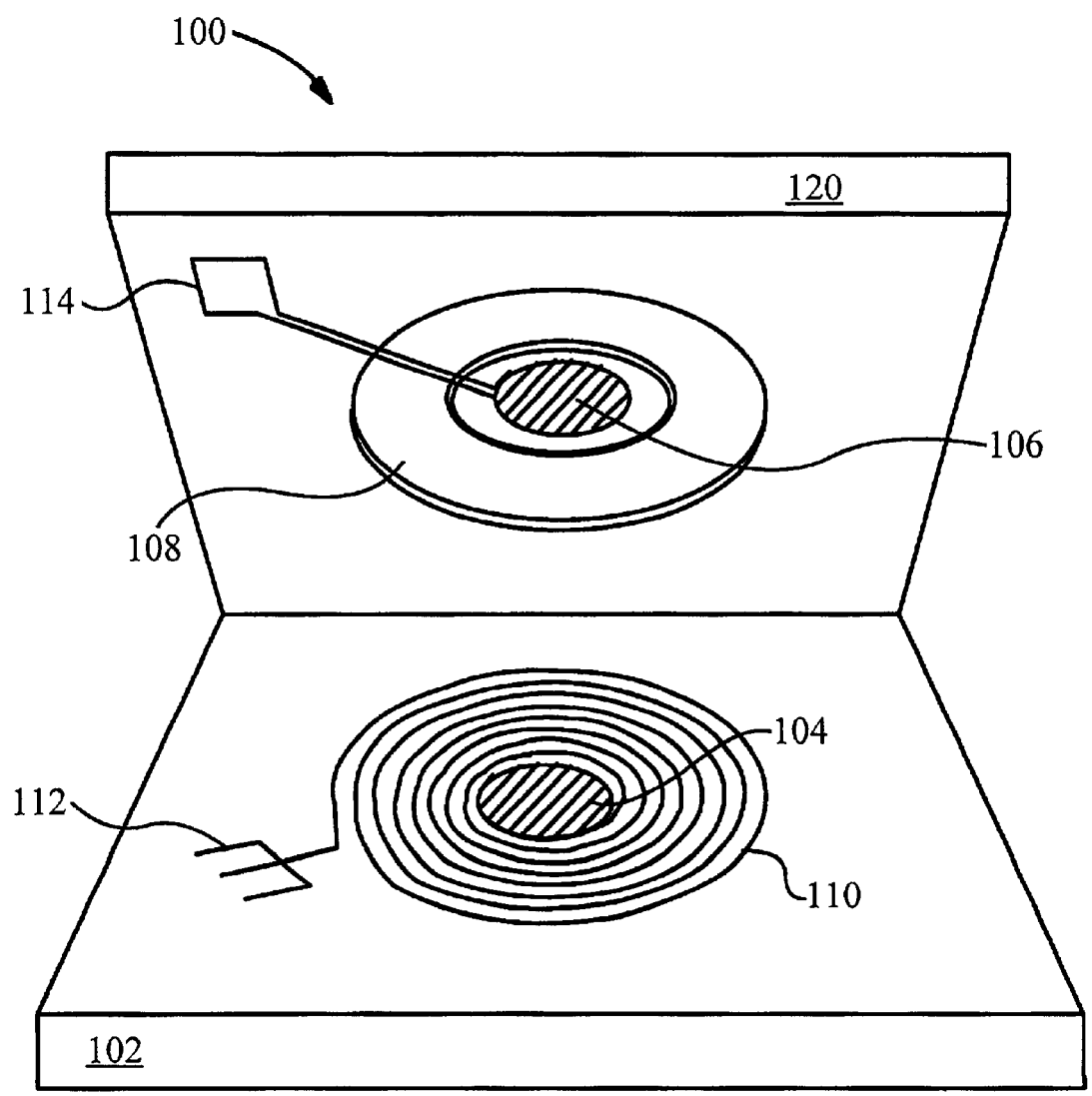
FIG. 1A is a split-level diagram of a pressure sensor according to a first embodiment of the present invention.

FIG. 1A shows a split-level view of a pressure sensor 100 according to a first embodiment of the present invention. Pressure sensor 100 comprises a lower capacitor plate 104, an upper capacitor plate 106, and an inductor 110. The inductor 110 is a micromachined flat spiral coil that spirals around the lower capacitor plate 104. Typically, the inductor 110 is coplanar with the lower capacitor plate 104, however this need not be the case. The upper capacitor plate 106, the lower capacitor plate 104, and the inductor 110 are typically made of Al, Au or Cu. The lower capacitor plate 104 and the flat inductor coil 110 are placed on top of a substrate 102, which may be a deformable or non-deformable membrane. The substrate 102 is typically made of glass.

Figure 1B:
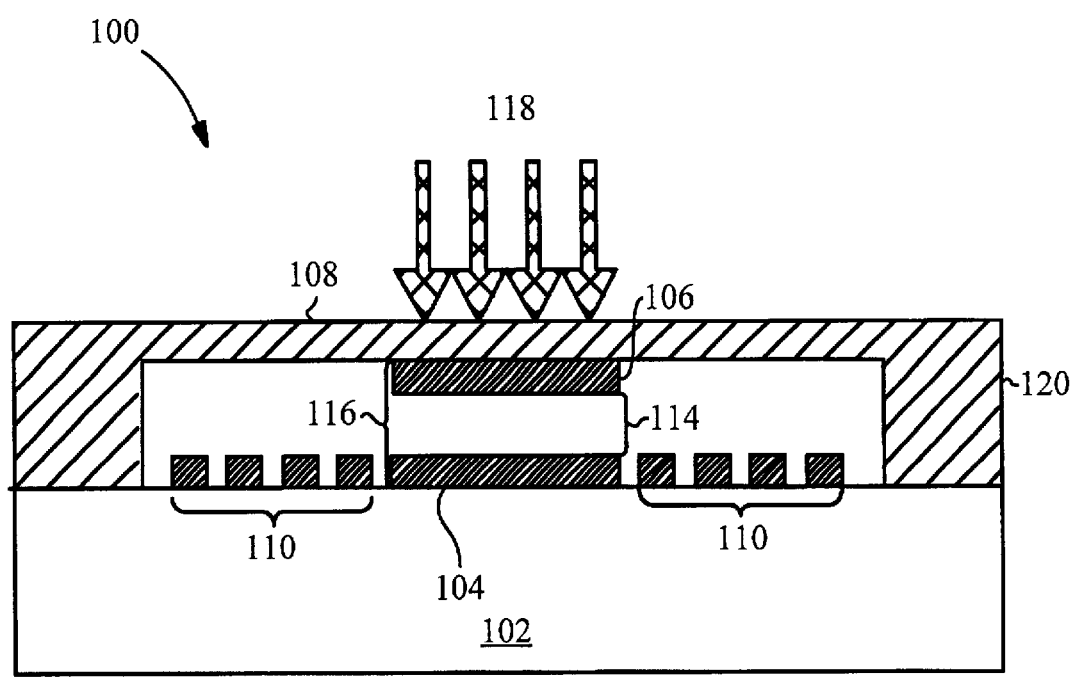
FIG. 1B is a cross-sectional diagram of the pressure sensor illustrated in FIG. 1A.
Figure 1C:
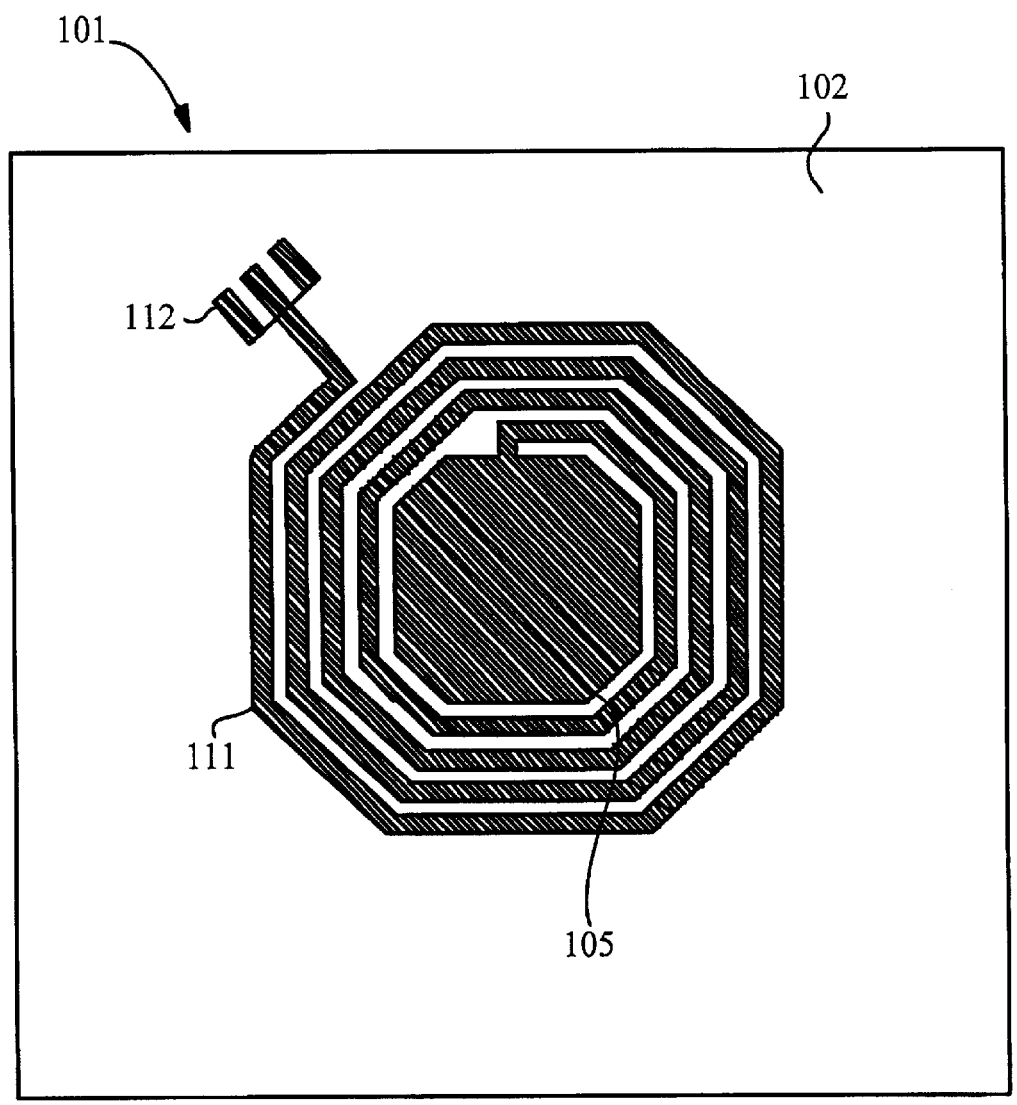
FIG. 1C is a diagram of the bottom side of the pressure sensor illustrated in FIG. 1A.

The pressure sensor 100 further includes a deformable membrane 108 bonded to the substrate 120. The membrane 108 is typically made silicon or of plastic materials including Silastic™, amorphous fluoropolymers such as Teflon™ AF, and polyimide such as Kapton. Kapton and Teflon are trademarks of the Dupont Corporation of Wilmington, Del. Silastic is a trademark of Dow Corning. The membrane 108 is placed on top of the upper capacitor plate 106. The lower capacitor plate 104 and the inductor 110 are coupled with the upper capacitor plate 106 through a lower contact point 112 and an upper contact point 114. A schematic diagram of an alternative layout of the lower side of a pressure sensor 101 is shown in FIG. 1C, which shows an octagonal spiral inductor 111 coiled in a coplanar fashion around the octagonal capacitor plate 105. The spiral inductor 111 may have other shapes such as circular, square, and others.

Figure 2A:
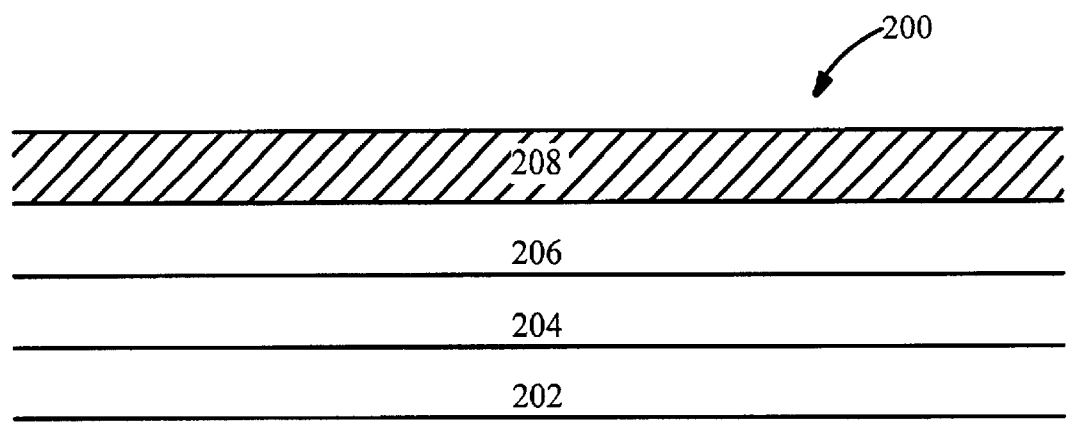
FIG. 2A–D are-cross-sectional schematic diagrams illustrating the steps of making a pressure sensor using a flexible circuit technique according to a second embodiment of the present invention.
Figure 2B:
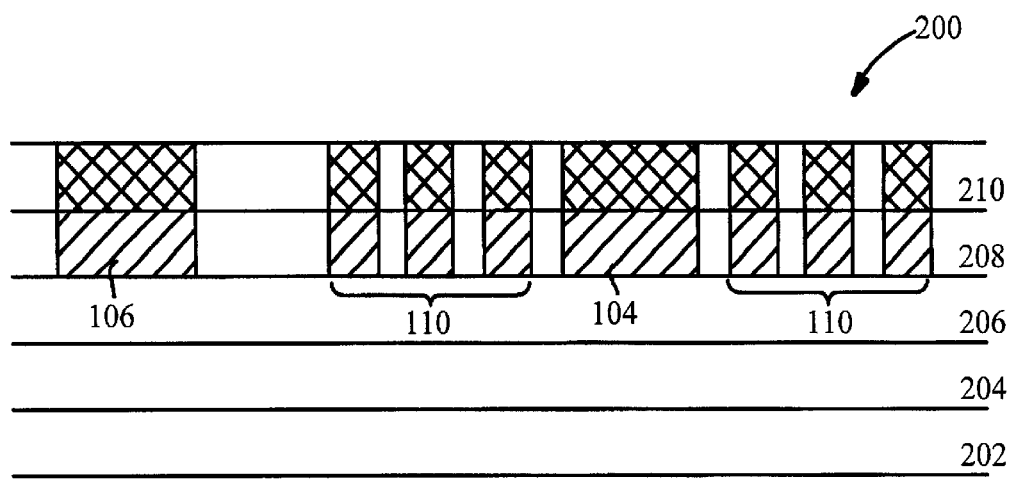
Figure 2C:
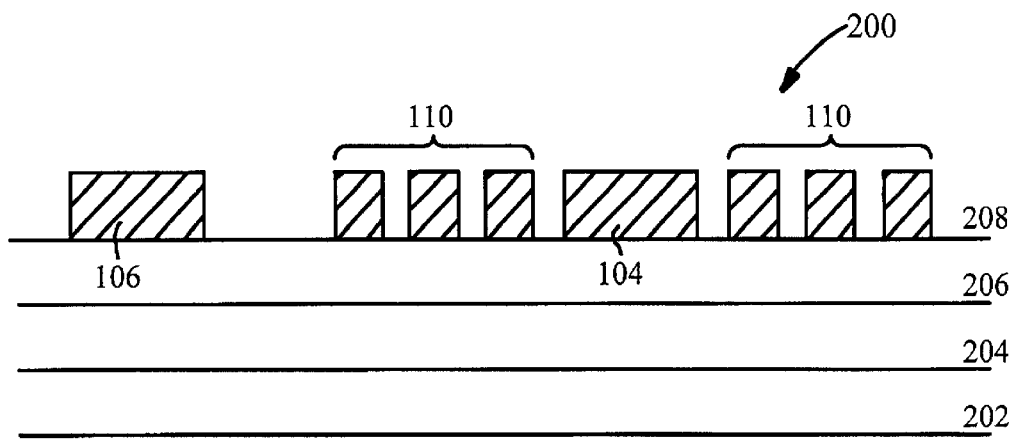
Figure 2D:
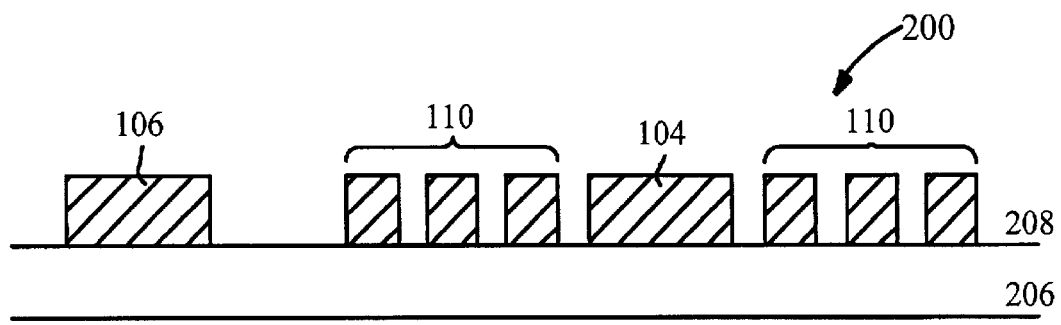
Figure 2E:
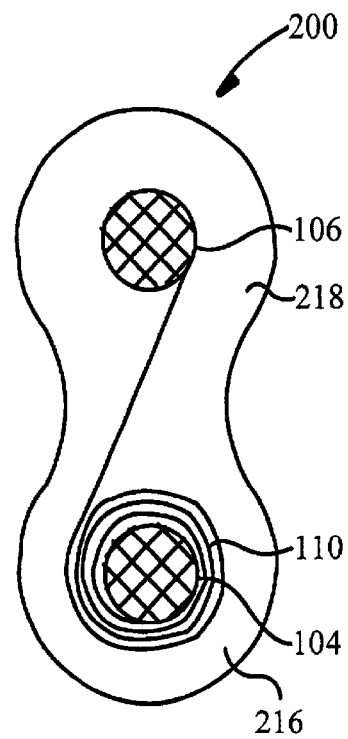
FIG. 2E is a diagram showing the top view of an unfolded dumb-bell shape of a pressure sensor illustrated in FIG. 2D.

The pressure sensor 100 illustrated in FIG. 1A may be produced using the flex circuit technology according to a second embodiment of the present invention. An exemplary embodiment of the process of fabricating a sensor such as the sensor 100 is shown in FIGS. 2A–2E. As shown in FIG. 2A, polymer film 206 including plastic materials as described above is spun. cast onto a 4-inch silicon wafer 202 coated with a thick release layer of aluminum 204. The silicon wafer 202 allows constructing polymer films 206 from about 5 μm to about 100 μm thick. A thin metal seed layer 208 of Cu or Au is sputtering deposited onto the polymer film 206. A photoresist layer 210 about 25–50 microns thick is spun cast onto the seed layer 208 and patterned to form the coil 110 and capacitor plates 104 and 106, as shown in FIG. 2B. The wafers 200 are placed into an Au plating path and Au is selectively plated up through the openings in the resist 210. The thin metal seed layer 208 is etched away from the areas between the plated metal coil 110 and the capacitor plates 104 and 106, and the photoresist layer 210 are stripped, as shown in FIG. 2C. A thin overcoating of a passivating material may be deposited, which. is not shown in FIG. 2C, with a choice range from spun cast polymers to plasma enhanced chemical vapor deposited silicon nitride or fluoropolymer. A thin masking layer is deposited over the overcoating layer, which is not shown in FIG. 2C, and patterned into the final dumb-bell shape of the unfolded sensor 200 with one circular plate 106 in the upper lobe 218 connected to the circular plate 104 and spiral coil 110 in the lower lobe 216 as shown in FIG. 2E. The spiral coil 110 has approximate lines and spaces of between about 25 microns and about 50 microns each. The polymer layer 206 is etched away exposing the release layer 204 below it. Release layer 204 is removed, and therefore the unfolded sensor 200 is freed from the silicon wafer 202, as shown in FIG. 2D. The sensor 200 is then placed into an assembly jig and the spacer layer is adhesively bonded to the lower lobe 216. Adhesive is placed over the upper lobe 218, and the upper lobe 218 is folded over the lower lobe 216, thus completing the sensor's structure 100, which is shown in FIG. 1A.

An alternative method of fabrication of the pressure sensor 100 uses a silicon Micro Electro Mechanical System (MEMS) approach, which is well known in the art. In this method, the deformable membrane 108 of the sensor 100 is made of silicon, and the silicon bearing the membrane is bonded to the underlying glass substrate 102 containing the lower capacitor plate 104 and the integrated micromachined inductor coil 110, as shown in FIG. 1B.

Figure 1D:
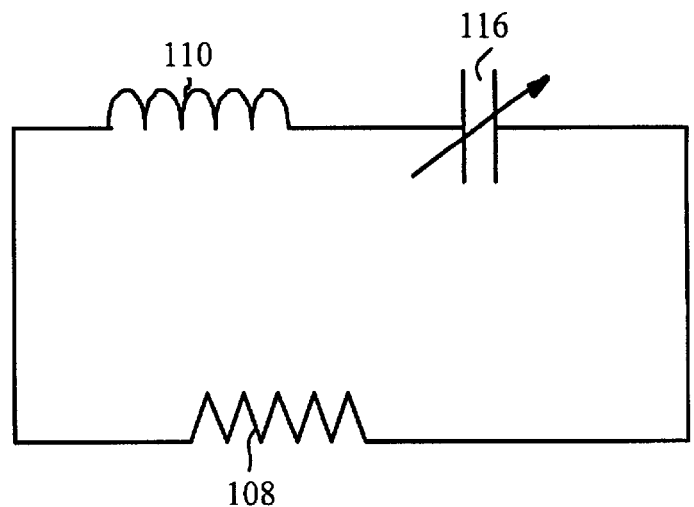
FIG. 1D is a schematic diagram illustrating a rough equivalent circuit to the LC circuit of the pressure sensor illustrating in FIG. 1A.

The pressure sensor 100 with the fully integrated capacitor 116 and inductor 110 may be miniaturized to a size less than 2×2×0.5 mm. The capacitor 116 and the inductor 110 are electrically coupled to each other, thereby forming a resonant LC circuit characterized by a resonant frequency. An external fluid, gas, or mechanical pressure 118 deflects the membrane 108 along with the upper capacitor plate 106, which varies the gap 124 of the capacitor 116. Thus, the capacitance value and the resonant frequency vary as functions of fluid pressure 118. In addition, the whole sensor 100 may be hermetically sealed. Fluid can not touch the sealed metal plates 104 and 106, so it can not form an electrical short between plates 104 and 106, which may produce an inaccurate pressure signal. If fluid touched the metal plate it would drastically lower the Q of the circuit, making measurements difficult if not impossible. Alternatively, if fluid got between plates there would be no pressure difference to deflect the plates. The Q value of the sensor 100 is typically about 10 or greater. A rough equivalent circuit of the resonant LC circuit of the pressure sensor 100 is shown in FIG. 1D. The resistor 108 of FIG. 1D represents the total of the resistive effects present in the sensor system.

Figure 3:
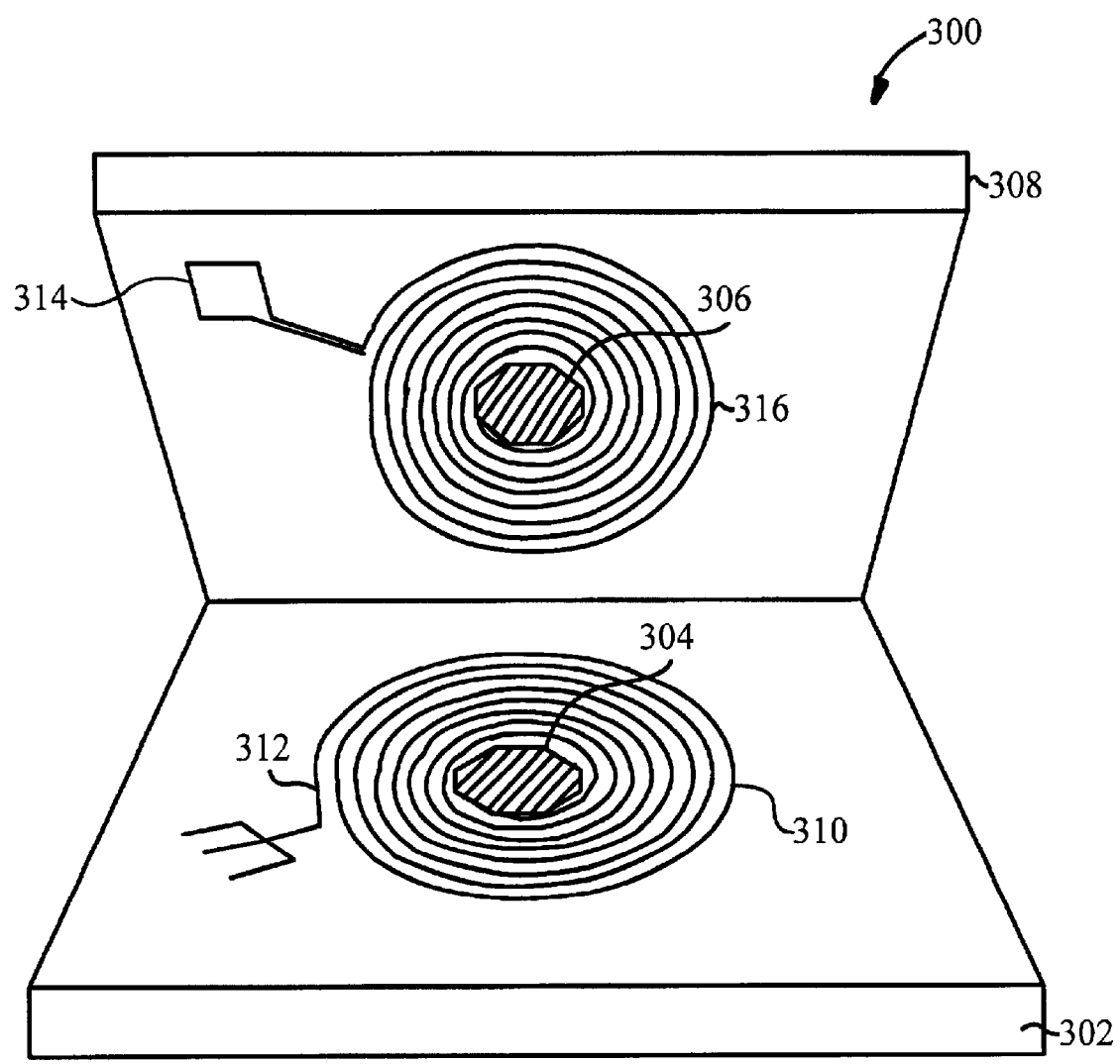
FIG. 3 is a cross-sectional diagram of an alternative pressure sensor.

An alternative pressure sensor 300 is shown in FIG. 3. The structure of pressure sensor 300 is typically similar to the structures of the pressure sensor 100 as described in FIG. 1A, except the pressure sensor 300 also includes another flat inductor coil 316, which is coplanar with the upper capacitor plate 306.

Figure 4A:
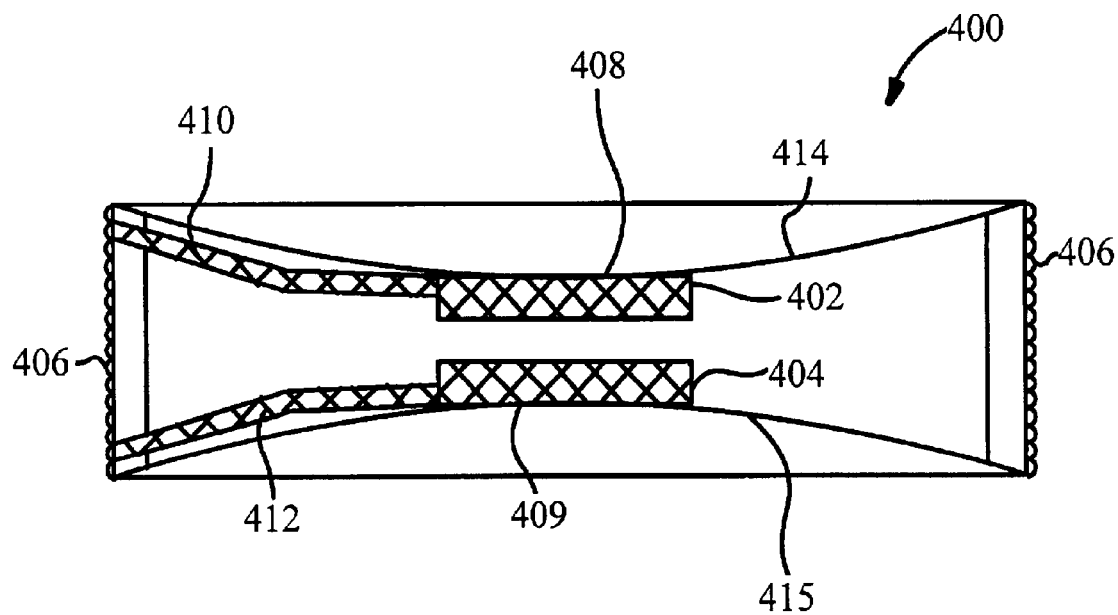
FIG. 4A is a cross-sectional diagram showing a diagrammatic view of another alternative pressure sensor.
Figure 4B:
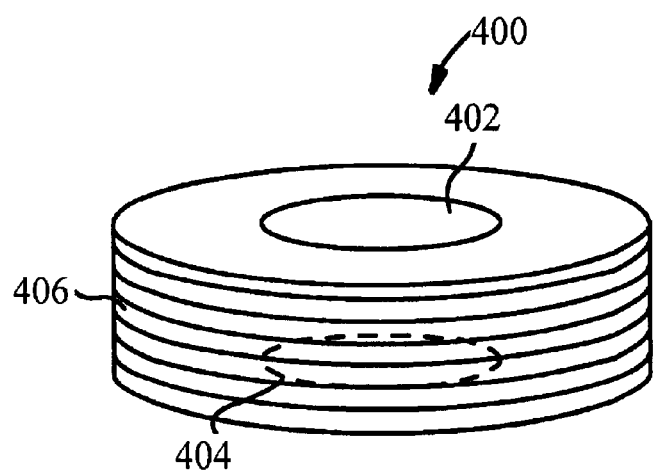
FIG. 4B is a diagram of the alternative pressure sensor illustrated in FIG. 4A.

Another alternative pressure sensor is shown in FIGS. 4A–B. FIG. 4A is a cross-sectional diagram of the pressure sensor 400. The pressure sensor 400 includes an upper capacitor plate 402 and a lower capacitor plate 404, which are made by removing selected portions of material from a sheet of conductive material such as a copper foil. A cylindrical spiral inductor coil 406 is coaxial with both capacitor plates 402 and 404. The cylindrical spiral inductor coil 406 may be formed from a sheet of conductive material, e.g., by wrapping the sheet around a cylindrical mandrel and removing selected portions of the sheet in a helical fashion. Material may be removed by any suitable technique, e.g., wet etch, plasma etch, laser milling, ion milling and the like. The mandrel may then be removed. The upper capacitor plate 402 is connected to the cylindrical inductor coil 406 by an upper connection 410, and the lower capacitor plate 404 is connected to the cylindrical inductor coil 406 by a lower connection 412. The upper capacitor plate 402 may be held in position by an upper silicone adhesive 408 connecting the capacitor plate 402 to an upper flexible membrane 414, which is disposed on top of the cylindrical spiral inductor coil 406. The lower capacitor plate 404 may be held in position by a lower silicone adhesive 409 connecting the lower capacitor plate 404 to a lower flexible membrane 415 disposed at the bottom of the cylindrical spiral inductor coil 406. A diagrammatic view of the pressure sensor 400 is shown in FIG. 4B.

Figure 5:
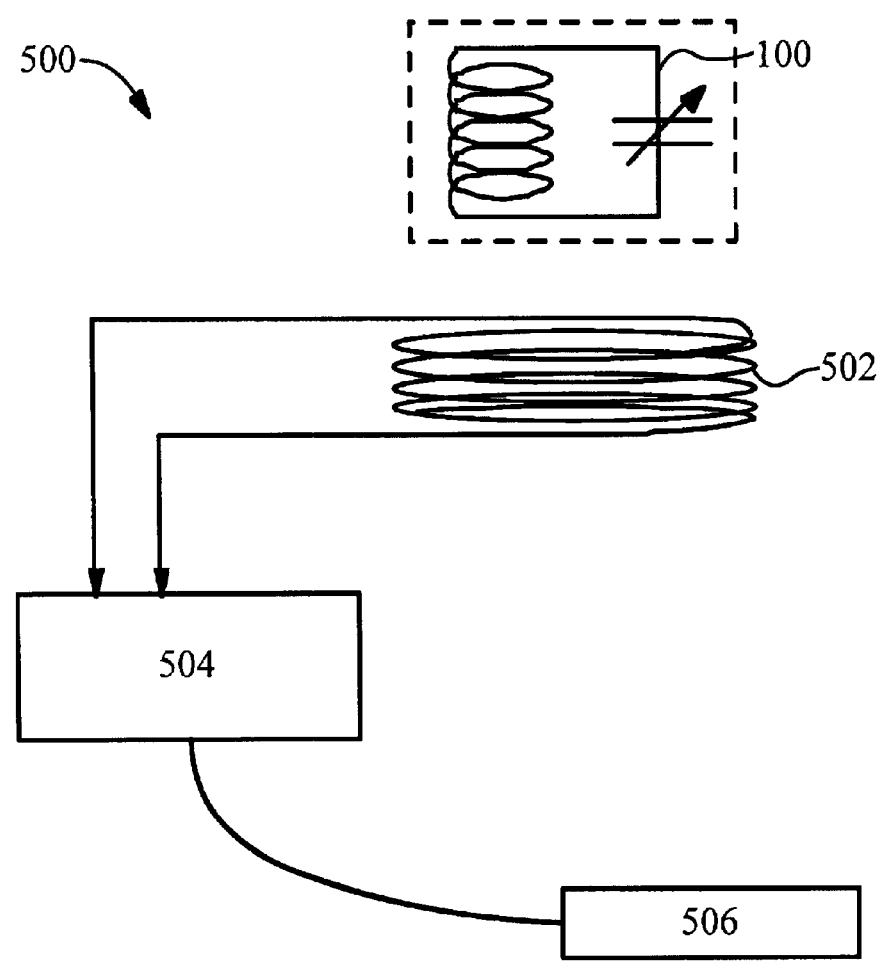
FIG. 5 is a diagram of an intraocular pressure sensor system.

Pressure sensors of the types depicted in FIGS. 1, 3 and 4 may be incorporated into a pressure measurement system, which is shown in FIG. 5. As shown in FIG. 5 a pressure measurement system 500 includes a pressure sensor 501 and an external detector pick-up coil 502 disposed proximate the sensor 501. The pressure measurement system 500 further includes an electronic interface module 504 coupled to the external detector pick-up coil 502, and a data analysis computer 506 coupled to the electronic interface module 504. The resonant frequency of the sensor 501 is a function of surrounding fluid pressure. The external detector pick-up coil 502 is a flat, wound coil having a diameter of about 2 cm. The external detector pick-up coil 502 is placed within about one centimeter of the sensor 501. In case of measuring intraocular pressure, the external detector pick-up coil 502 is placed in a device that can be worn safely, comfortably and conveniently without disturbance of vision or ocular physiology, such as being mounted within a pair of eyeglasses. The electronic interface module 504 could be a hand-held module.

To measure intraocular or intra-tissue pressures, the sensor 501 is inserted into a tissue or organ. The deformable membrane disposed on top of one capacitor plate of the IOP sensor 501 is a thin, flexible diaphragm. The deflection of the capacitor plate depends on the pressure applied to the diaphragm. The higher the pressure, the lager the deflection. These pressure-induced motions of the diaphragm change the value of the capacitor element, which, in turn, change the resonant frequency of the LC circuit. An increase in pressure causes an increase in capacitance, which causes a decrease in resonant frequency.

The resonant frequency of the sensor 501 is detected by applying a signal to the external detector pick-up coil 502. The signal applied to the external detector pick-up coil 502 is varied in frequency until the resonant frequency of the sensor 501 is located. Since the implanted device depends on no external energy for operation (and then only during interrogation), there are no concerns about implantable power sources such as batteries.

The signal applied to the external detector pick-up coil 502 is generated by an electronic interface module 504, which is controlled by a data analysis computer 506. The resonant frequency of the sensor 501 is detected by the electronic interface module 504 and transmitted to the data analysis computer 506 for analysis and calibration. In this way, the intraocular pressure may be measured on a continuous basis.

To measure the intraocular pressure, an intraocular pressure (IOP) sensor has features in common with the sensors depicted in FIGS. 1, 3 and 4 can be placed in the anterior chamber, posterior chamber, vitreous cavity, or within the tissues and intracellular spaces in the eye. The IOP sensor also can be placed, in the orbital space, or within tubes attached to the eye or its contents, in or along with drainage tubes, shunts or setons.

Figure 6A:
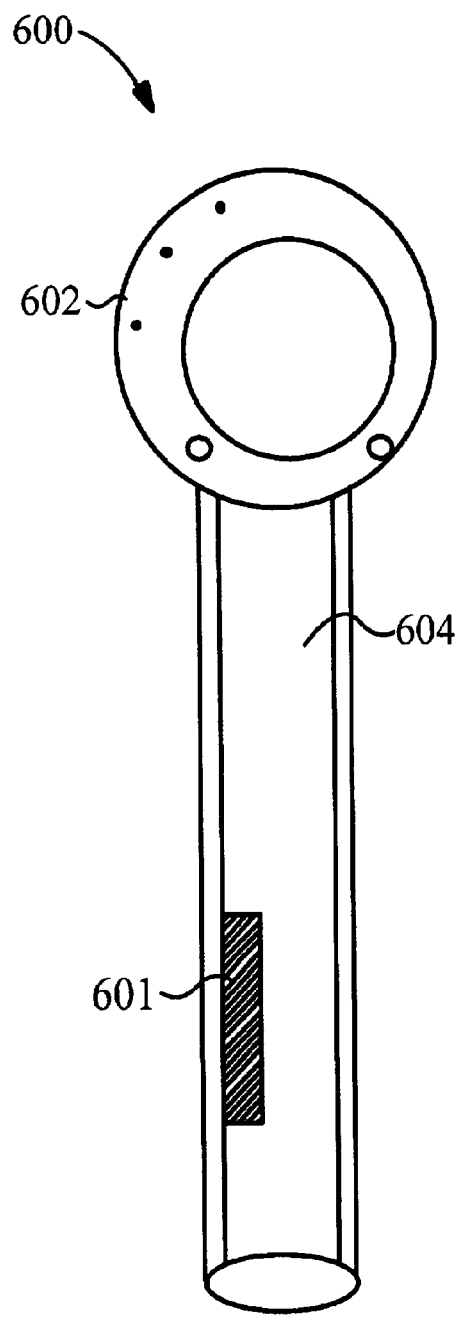
FIG. 6A–B are cross-sectional view and view facing sensor from inside of a glaucoma shunt.
Figure 6B:
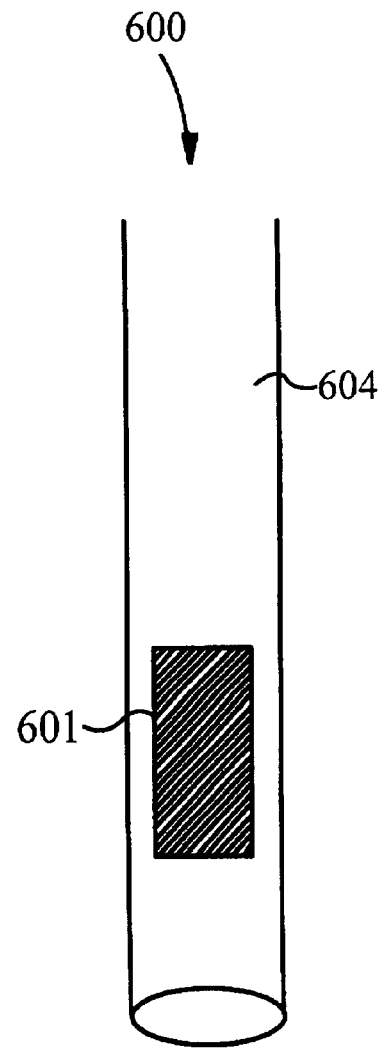

FIGS. 6A–B are schematic diagrams of a glaucoma shunt device 600 with an attached pressure sensor 601, which is used to implant a pressure sensor into an eye. Sensor 601 typically has features in common with the sensors depicted in FIGS. 1, 3 and 4. The device 600 includes a reservoir/plate 602 and a tube 604 leading to the reservoir/plate 602. The pressure sensor 601 is placed inside the tube 604. FIG. 6A is a cross-section view of the device 600, and FIG. 6B depicts a view-facing sensor 601 from inside the tube 604.

Figure 7:
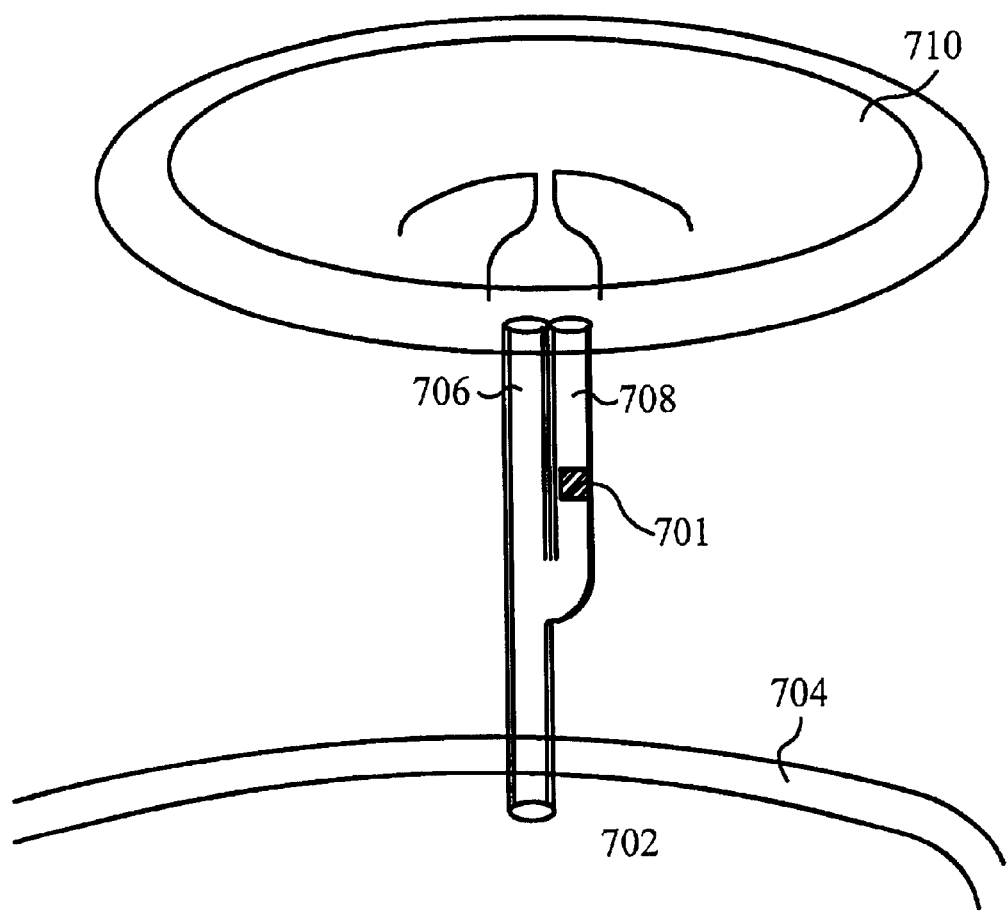
FIG. 7 is a diagram of another glaucoma shunt implant with attached pressure sensor.

FIG. 7 shows a schematic diagram illustrating of using a glaucoma shunt (setons, tubes, or valves) to insert a pressure sensor into an eye. As shown in FIG. 7, a pressure sensor 701 of the type depicted in FIGS. 1, 3 and 4 is attached or placed within the lumen of an adjoining barrel 708 running parallel; to the drainage tube 706. The barrel 708 houses the sensor and open to the side of the lumen of the drainage tube 706. The tube 706 and the second barrel 708 are connected to the glaucoma shunt/reservoir 710. The tube 706 is inserted into the anterior chamber 702 of an eye. In this case the sensor 701 sits outside of the anterior chamber 702, but it is able to measure the intraocular pressure within the lumen of the tubes 706 and 708.

Figure 8:
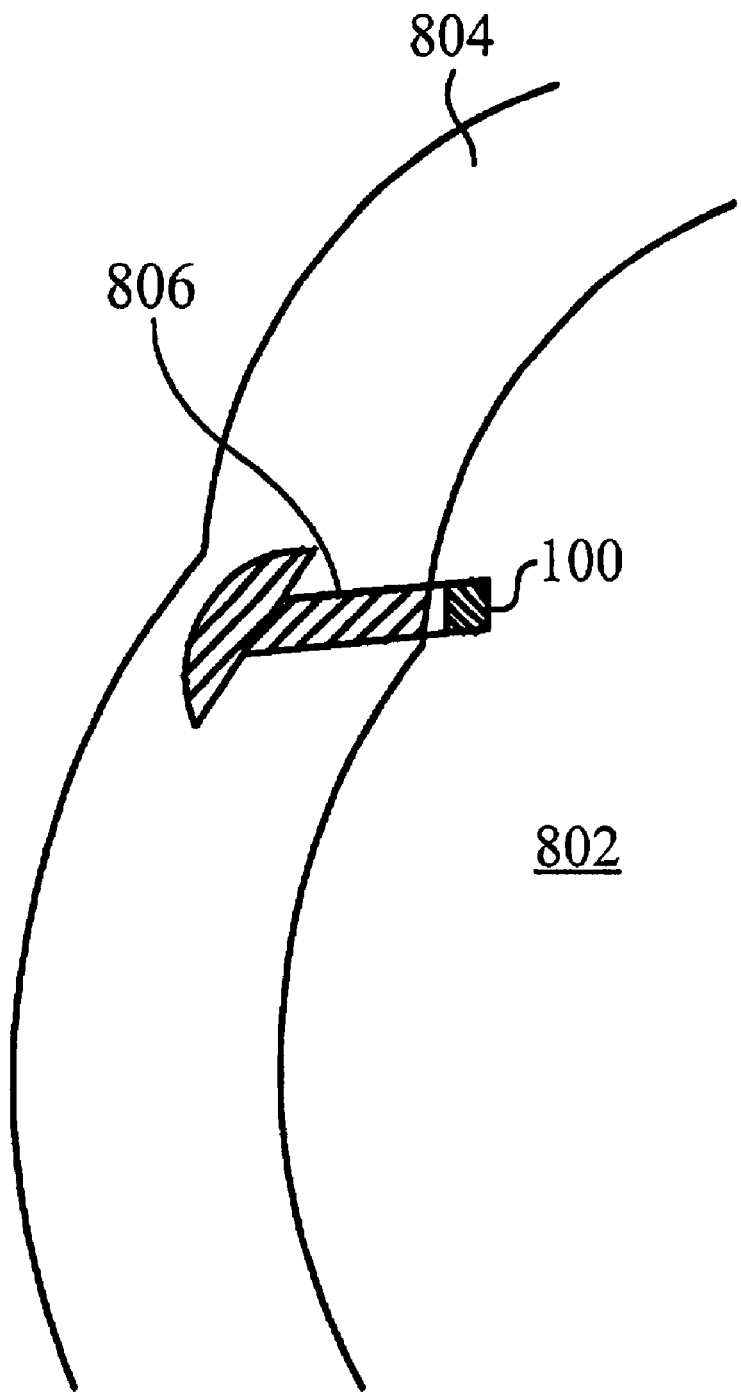
FIG. 8 is a diagram of a nail-shaped bio-compatible material implant with attached pressure sensor.

An IOP sensor such as the sensor 100 also can be inserted into an eye by using a nail-shaped implantable device, which is shown in FIG. 8. The IOP sensor 100 is attached to the nail's tip device 806. The device 806 is inserted in the inner layer of the cornea 804 by a surgical implantation. The tip of the device 806 with the attached sensor 100 sits inside of an anterior chamber 802 of an eye that is not shown in FIG. 8.

It will be clear to one skilled in the art that the above embodiment may be altered in many ways without departing from the scope of the invention. For example, pressure sensors 100, 300, 400 may be typically coated with a medical-grade biocompatible coating, such as Silastic™, prior to being used for implantation. These pressure sensors may be used to measure intraocular pressure, intravascular pressure, intracranial pressure, pulmonary pressure, biliary-duct pressure, blood pressure, pressure in joints, and pressure in any body tissue of fluid. These pressure sensors may find application in blood pressure monitoring systems, vital signs monitoring systems, respiratory health maintenance apparatus applications, such as spirometers and oxygen therapy equipment, sleep labs and sleep apnea monitoring systems, and drug delivery systems. These pressure sensors may also be incorporated with any surgical equipment, where intratubal pressure readings (positive or negative pressure.) are necessary during surgical procedures, or where intratubal pressure readings are representative, or relative to the pressure readings within the body, or body cavity, organ, or tissue.

Pressure sensors 100, 300 and 400 can be used for measurement of pressure in non-medical pressurized chambers or cavities. For example, it can be used to measure the pressure in tires of a vehicle such as a passenger automobile, airplane, truck or bus.

Pressure sensors 100, 300 and 400 can be used in combination with equipment, where precise pressure control and monitoring is important, such as drug delivery systems or pressure release valves and mechanisms. For example, these pressure (sensors can be placed inside a champagne bottle to check the pressure inside, so pressure is released by a rubber valve at the bottom of the champagne bottle when pressure inside of the bottle reaches high levels that cause the bottle popping. Accordingly, the scope of the invention should be determined by the following claims and their legal equivalents.

What is claimed is:

1. A continuous pressure sensing apparatus comprising an inductor/capacitor resonant means, the inductor/capacitor resonant means including:
   a) at least one first spiral inductor coil having a first end and a second end;
   b) at least one first capacitor plate connected to the first end of the first spiral inductor coil, wherein the first spiral inductor coil and the first capacitor plate are made by removing selected portions of material from a conductive sheet;
   c) a second capacitor plate disposed proximate the first capacitor plate; and
   d) a second spiral inductor coil connected to the second capacitor plate and the second end of the first spiral inductor coil.

2. The apparatus of claim 1, wherein the first spiral inductor coil is a flat coil.

3. The apparatus of claim 2, wherein the first capacitor plate, the second capacitor plate, and the first flat spiral inductor coil comprise metal films selected from the group consisting of Al, Au, and Cu.

4. The apparatus of claim 2, wherein the first capacitor plate is attached to a substrate.

5. The apparatus of claim 4, further comprising a deformable membrane bonded to the substrate.

6. The sensor of claim 5, wherein the deformable membrane is made of a material selected from the group consisting of silicon, plastic, amorphous fluoropolymers, and polyimide.

7. The apparatus of claim 6, wherein the deformable membrane is located on top of the second capacitor plate.

8. The apparatus of claim 7, wherein the deformable membrane is deflected relative to the second capacitor plate by fluid, gas, or mechanical pressure, whereby the capacitance between the first and second capacitor plates varies.

9. The apparatus of claim 2, wherein the first capacitor plate, the second capacitor plate, and the first spiral inductor coil comprise a hermetically sealed unit.

10. The apparatus of claim 9, wherein the first spiral inductor coil is coupled to the first and second capacitor plates.

11. The apparatus of claim 10, wherein the first spiral inductor coil is coplanar with the first capacitor plates.

12. The apparatus of claim 11, wherein the first spiral inductor coil is coaxial with the first capacitor plate.

13. The apparatus of claim 12, wherein the second spiral inductor coil is a flat coil that is coplanar with the second capacitor plate.

14. The apparatus of claim 12, wherein the second spiral inductor coil is coaxial with the second capacitor plate.

15. A continuous pressure sensing apparatus comprising an inductor/capacitor resonant means, the inductor/capacitor resonant means including:
   a first capacitor plate;
   a second capacitor plate disposed proximate the first capacitor plate;
   an inductor coil connecting the first capacitor plate and the second capacitor plate,
   wherein the first capacitor plate, the second capacitor plate and the first inductor coil comprise a hermetically sealed unit, and
   wherein the inductor coil is in a separate plane than the first and second capacitor plates.

16. The apparatus of claim 15, wherein the inductor coil is a cylindrical coil.

17. The apparatus of claim 16, wherein the cylindrical coil is coaxial with the first and second capacitor plates.

18. The apparatus of claim 1, wherein the inductor/capacitor resonant means is characterized by a resonant frequency.

19. The apparatus of claim 18, wherein the inductor/capacitor resonant means has a Q value of about 10 or greater.

20. The apparatus of claim 18, wherein the resonant frequency is a function of fluid, gas or mechanical pressure.

21. A pressure measurement system comprising:
   a) a pressure sensor having an inductor/capacitor resonant circuit, the inductor/capacitor resonant circuit including:
      i) at least one first spiral inductor coil having a first end and a second end; and
      ii) at least one first capacitor plate connected to the first end of the first spiral inductor coil;
      wherein the first spiral inductor coil and the first capacitor plate are made by removing selected portions of material from a flat conductive sheet; and
   b) a remote external detector pick-up coil disposed proximate the pressure sensor.

22. The system of claim 21, wherein the sensor is coated with a medical-grade biocompatible coating.

23. The apparatus of claim 1, wherein the apparatus has a length less than 2 mm, a width less than 2 mm, and a thickness less than 0.5 mm.

24. The system of claim 21, further comprising means for inserting the sensor in an eye to measure intraocular pressure.

25. The system of claim 24, wherein the inserting means is capable of placing the sensor in an anterior chamber, posterior chamber, vitreous cavity, or within tissues or intercellular spaces in the eye.

26. The system of claim 24, wherein the inserting means is capable of placing the sensor in an orbital space, or within tubes attached to the eye or its contents, in or along with drainage tubes, shunts, or setons.

27. The system of claim 24, wherein the sensor is incorporated into a contact lens adapted to contact the cornea or sclera of an eye.

28. The system of claim 21, further comprising an electronic interface module coupled to the external detector pick-up coil.

29. The system of claim 28, wherein the electronic interface module is a hand-held module.

30. The system of claim 29, further comprising a data analysis computer coupled to the electronic interface module.

31. The system of claim 21, wherein a resonant frequency of the inductor/capacitor resonant circuit changes with external pressure.

32. The system of claim 21, wherein the external detector pick-up coil is a flat coil having a diameter of about 2 cm.

33. The system of claim 32, wherein the sensor and the detector pick-up coil are adapted to measure an intraocular pressure.

34. The system of claim 33, wherein the external detector pick-up coil is mounted within a pair of eyeglasses.

35. The apparatus of claim 15, wherein the first capacitor plate is attached to a substrate.

36. The apparatus of claim 35, further comprising a deformable membrane bonded to the substrate, wherein the deformable membrane is made of a material selected from the group consisting of silicon, plastic, amorphous fluoropolymers, and polyimide.

37. The apparatus of claim 36, wherein the deformable membrane is located on top of the second capacitor plate.

38. The apparatus of claim 37, wherein the deformable membrane is deflected relative to the second capacitor plate by fluid, gas, or mechanical pressure, whereby the capacitance between the first and second capacitor plates varies.

39. The apparatus of claim 15, wherein the inductor/capacitor resonant means is characterized by a resonant frequency and wherein the resonant frequency is a function of fluid, gas or mechanical pressure.

40. The apparatus of claim 15, wherein the inductor/capacitor resonant means has a Q value of about 10 or greater.

41. The apparatus of claim 15, wherein the apparatus has a length less than 2 mm, a width less than 2 mm, and a thickness less than 0.5 mm.

* * * * *